US00PP08057P

United States Patent [19]

Gerawan

[11] Patent Number: Plant 8,057

[45] Date of Patent: Dec. 8, 1992

[54] PRIMA RED PLUM 9-1

[76] Inventor: Michael R. Gerawan, 6407 S. Englehart, Reedley, Calif. 93654

[21] Appl. No.: 633,294

[22] Filed: Dec. 24, 1990

[51] Int. Cl.[5] ..... A01H 5/00

[52] U.S. Cl. ..... Plt./38.1

[58] Field of Search ..... Plt./38

*Primary Examiner*—James R. Feyrer

*Attorney, Agent, or Firm*—Worrel & Worrel

[57] ABSTRACT

A new and distinct variety of plum tree producing fruit of reddish coloration which are mature for harvesting and shipment approximately the second week in September in the San Joaquin Valley of central California approximately seven days prior to the fruit produced by the "Roysum" plum tree and which have a pleasing low acid taste with a distinct depression in the suture and good shipping and handling characteristics.

1 Drawing Sheet

BACKGROUND OF THE NEW VARIETY

The present invention relates to a new and distinct variety of plum tree, hereinafter be denominated varietally as the "Prima Red Plum 9-1" plum tree, and more particularly to a plum tree which produces semi-freestone fruit of large size having a pleasing, slightly acidic flavor, a distinctive oblate form, a reddish skin coloration and flesh of a cream coloration and which is mature for harvesting and shipment approximately the second week of September in the San Joaquin Valley of central California.

Tree fruit varieties in which the fruit matures relatively late in the season frequently possess characteristics which are less desirable than varieties maturing more near the middle of the season. Thus, less attractive size, flavor, coloration, shelf life and the like are tolerated since the fruit may be one of only several varieties available at that point in the harvest season. As a consequence, effort is continually devoted to developing tree fruit varieties which produce fruit which matures relatively late in the harvest season and yet which possesses attributes more closely paralleling those of fruit varieties maturing earlier in the season.

The plum tree of the instant variety is particularly promising in that it produces semi-freestone fruit of large size and pleasing skin and flesh coloration maturing relatively late in the season, that is in the second week of September in the San Joaquin Valley of central California or about seven to ten days after the fruit of the "Angeleno" plum tree and about one week prior to the fruit of the "Roysum" plum tree. The fruit is characterized by a pleasing, slightly acidic flavor with a juicy, meaty texture.

ORIGIN AND ASEXUAL REPRODUCTION OF THE NEW VARIETY

The plum tree was discovered in 1984 by the inventor in a cultivated area on Ranch 2 owned by Ray and Star Gerawan located in Sanger in the San Joaquin Valley of central California. The new variety was discovered as an open pollinated seedling as the result of a mass breeding program. The seedling was selected from this program, but its parentage is unknown. Seeds collected for the mass breeding program came from several ranches encompassing nearly five thousand acres growing many varieties of tree fruit. No effort was made to retain the specific pedigree of any particular seed lot. The new variety was asexually reproduced by grafting and budding test trees to the new variety on Ranches 2, 12 and 16 owned by Ray and Star Gerawan. The inventor has continuously observed the test trees of the new variety and has confirmed that the progeny possess the same characteristics as the parent tree of the new variety.

SUMMARY OF THE NEW VARIETY

The "Prima Red Plum 9-1" plum tree is characterized as to novelty by producing semi-freestone fruit which has a dark reddish skin coloration and is of large size with a very distinct suture depression and a flat or depressed apex. The fruit has a pleasing, slightly acidic flavor with a juicy, meaty texture and is ripe for commerical harvesting and shipment approximately the second week in September in the San Joaquin Valley of central California.

BRIEF DESCRIPTION OF THE DRAWING

The accompanying drawing is a photograph showing the plum tree of the new variety including fruit of the new variety sectioned, one with the stone in place and the other with the stone removed to expose the pit cavity; a second in tip plan view showing the apex end thereof; a third in top plan view with its natural waxy coating left in place; a fourth in bottom plan view showing its base; a fifth in side elevation showing its suture; a stone of the new variety; a portion of a branch; and representative foliage of the new variety.

DETAILED DESCRIPTION

Referring more specifically to the pomological details of this new and distinct variety of plum tree, the following has been observed under the ecological conditions prevailing at a ranch which is located in Sanger, Calif. All major color code designations are by reference to the Dictionary of Color, by Maerz and Paul, First Edition, 1930. Common color names are also employed occasionally.

TREE

Generally:

*Size.*—Medium.

*Figure.*—Upright. The subject variety is upright to upright-spreading in form and relatively dense. The asexually reproduced trees were pruned so that each tree has a standard vase-shaped configuration.

*Productivity.*—Productive.

*Regularity of bearing.*—Regular.

Trunk:

*Size.*—Stocky.

*Surface texture.*—Medium shaggy.

Branches:

*Size.*—Medium.

*Surface texture.*—Medium shaggy.

*Color.*—Base — 39, Plate 8 E-11 Pickaninny, Periquet otter. Streaks — Page 35, Plate 6, B-12 Gypsy.

*Lenticels.*—Numbers — numerous. Size — 1 mm (0.04 inches) by 4 mm (0.16 inches) to 7 mm (0.28 inches).

LEAVES

Size:

*Generally.*—Medium.

*Average length.*—100 mm (4 inches) to 105 mm (4.2 inches).

*Average width.*—40 mm (1.6 inches) to 45 mm (1.8 inches).

Shape: Ovate.

Color:

*Upwardly disposed surface.*—Page 69, Plate 23, J-11, Cossack Green.

*Downwardly disposed surface.*—Page 63, Plate 20, C-9, Peacock Gr.

Marginal form: Serrate.

Glands: None.

Petiole:

*Length.*—15 mm (0.6 inches) to 17 mm (0.68 inches).

*Thickness.*—2 mm (0.08 inches).

Stem glands:

*Number.*—From none to three.

*Arrangement.*—Opposite when there are two stem glands.

Stem glands:

*Size.*—Small.

*Type.*—Globose.

*Color.*—Green.

Stipules: None.

FLOWERS

The following description was taken from bloom of trees of the subject variety growing in a test planting near Sanger, Calif. in early March, 1992. The number of chilling hours below 45 degrees Fahrenheit in this fruit growing area of Fresno County, Calif. in the 1991–1992 winter season was nearly 1200 hours. This represents an above average accumulation of cold hours for this location.

Flower buds:

*Size.*—Medium, conic in form, plump and slightly appressed to the stem. The buds are hardy under typical climatic conditions in the San Joaquin Valley of California.

*Surface texture.*—Flower buds — Scales — Color — Medium brown. Piccadilly Brown (7-H-10).

Pedicel: Short.

Stamens: Numerous.

Pistil: One.

Date of bloom: Two to three days ahead of "Santa Rosa" plum tree and about the same time as the "Blackamber" plum tree. The bloom is early in timing in relation to other standard plum varieties. The bloom is approximately at the same time as the "Blackamber" plum tree and slightly after the "Ambra" plum tree. In 1992 the date of first bloom of the new variety was February 23 and the date of full bloom was February 27. No pollination tests have been conducted, but it is believed the new variety requires pollination as in conventional varieties. This is achieved by proximity to other varieties blooming at the same time such as the "Blackamber" plum tree.

Flower:

*Size.*—Medium.

*Diameter.*—Fully expanded averages from 19 mm (0.7480 inches) to 22 mm (0.8661 inches). At full expansion the petals are slightly cupped inwards.

Bloom:

*Quantity.*—Abundant.

Flower buds:

*Number.*—Varies from 4 to 6 per node.

Petals:

*Number.*—Five.

*Size.*—Medium.

*Length.*—Averaging from 8 mm (0.3149 inches) to 10 mm (0.3937 inches).

*Width.*—6 mm (0.2362 inches) to 7 mm (0.2755 inches).

*Shape.*—Variable from oval to obovate in form.

*Color.*—White (1-A-1).

Petal claw:

*Form.*—Truncate and very short.

Petal margins: Substantially undulate, especially at the apex and over the apical shoulders.

Petal apices: Generally rounded.

Pedicel: Moderately long from 6 mm (0.2362 inches) to 8 mm (0.3149 inches).

*Thickness.*—Averages 1.0 mm (0.0393 inches).

*Color.*—Light green (17-J-3).

Pedicel surface: Variable, most frequently glabrous, but occasionally a few short hairs are present, usually basally.

Calyx:

*Surface.*—*Glabrous.*

*Color.*—Light green (19-J-2) with slight tinge of brown.

Nectaries:

*Color.*—Light brown-orange (Burnt Brown 12-K-6) when young, darkening to a dull orange-brown (Gold Pheasant 13-L-12) with age.

Anthers:

*Size.*—Medium.

*Color.*—Yellow-orange (Corn Yellow 10-J-5) ventrally, but with red (Pompeian Red 4-J-10) margins dorsally.

Pollen: Abundant.

*Color.*—Yellow (Chinese yellow 10-K-6).

Stamens:

*Length.*—Variable in relation to pistil from longer than pistil to about equal. From 5 mm (0.1968 inches) to 7 mm (0.2755 inches).

*Color.*—White (1-A-1).

Pistils:

*Length.*—From 6 mm (0.2362 inches) to 7 mm (0.2755 inches) including the ovary.

*Color.*—Light yellow-green (17-H-2).

FRUIT

Maturity when described: Ripe for commercial harvesting and shipment approximately the second week of September near Sanger, Calif., and about seven to ten days after the "Angeleno" plum tree and about one week ahead of the "Roysum" plum tree. The new variety requires thinning as in other varieties of plum trees.

Size:

*Average diameter.*—73 mm (2.92 inches) to 80 mm (3.2 inches).

*Average diameter transverse in the suture plane.*—73 mm (2.92 inches) to 77 mm (3.08 inches).

*Average diameter transverse and at right angles to the suture plane.*—55 mm (2.2 inches) to 60 mm (2.4 inches).

*Form.*—Uniformity — Uniform. Symmetry — Oblate.

*Suture.*—Generally — Distinct, depressed 2 mm (0.08 inches) to 3 mm (0.12 inches) throughout. Length— 95 mm (3.8 inches) to 105 mm (4.2 inches).

*Ventral surface.*—Generally — Smooth.

Stem cavity.—Generally — Obtuse. Depth — 32 mm (1.28 inches) by 40 mm (1.6 inches) by 12 mm (0.48 inches).

*Stem.*—Length — 12 mm (0.08 inches). Caliper— 3 mm (0.12 inches).

*Apex.*—Shape — Some flat, some depressed.

Base.—Some flat, some retuse.

Pistil point.—Flattened.

Skin:

*Thickness.*—Medium.

*Texture.*—Medium. Surface of fruit is pebbly.

*Tendency to crack.*—None.

*Color.*—Page 133, Plate 55, L-12, Vineyard Oporjof.

*Pubescence.*—None.

Flesh:

Color.—Page 41, Plate 9, D-2, Cream.

*Surface of pit cavity.*—Smooth.

*Color of pit well.*—Same as flesh.

*Amygdalin.*—None.

*Juice production.*—Juicy.

*Flavor.*—Slightly acid and pleasing. The flavor is sweet and relatively mild with low acidity.

*Aroma.*—None.

*Texture.*—Meaty.

*Fibers.*—Numbers — Moderate.

*Ripening.*—*Even.*

*Eating quality.*—Good. The fruit is crisp and juicy at full maturity.

Stone:

*Attachment.*—Semi-freestone.

*Fibers.*—*Numbers — A few adhering to edges.*

*Size.*—Length — 20 mm (0.8 inches). Width — 16 mm (0.64 inches). Thickness — 9 mm (0.36 inches).

*Form.*—Generally — Oval.

*Color.*—Page 45, Plate 11, J-7, Inca Gold.

*Base.*—Shape— Indented 2 mm (0.08 inches) where stem attaches.

*Sides.*—Generally — Smooth.

*Ridges.*—None.

*Grooves.*—None.

*Dorsal edge.*—Narrow with slight groove throughout.

*Ventral edge.*—Slight wing from base to middle of pit.

*Tendency to split.*—None.

Use: Fresh.

Keeping quality: Good.

Shipping and handling qualities: Good.

Although the new variety of plum tree possesses the described characteristics noted above as a result of the growing conditions prevailing near Sanger in the central San Joaquin Valley of California, it is to be understood that variations of the usual magnitude and characteristics incident to changes in growing conditions, fertilization, irrigation, pruning and pest control are to be expected.

Having thus described and illustrated my new variety of plum tree, what I claim as new and desire to be secured by Plant Letters Patent is:

1. A new and distinct variety of plum tree substantially as illustrated and described and which produces a semi-freestone fruit of reddish coloration with cream colored flesh which are mature for commercial harvesting and shipment approximately the second week of September in the San Joaquin Valley of central California, about seven days before the "Roysum" plum tree.

* * * * *

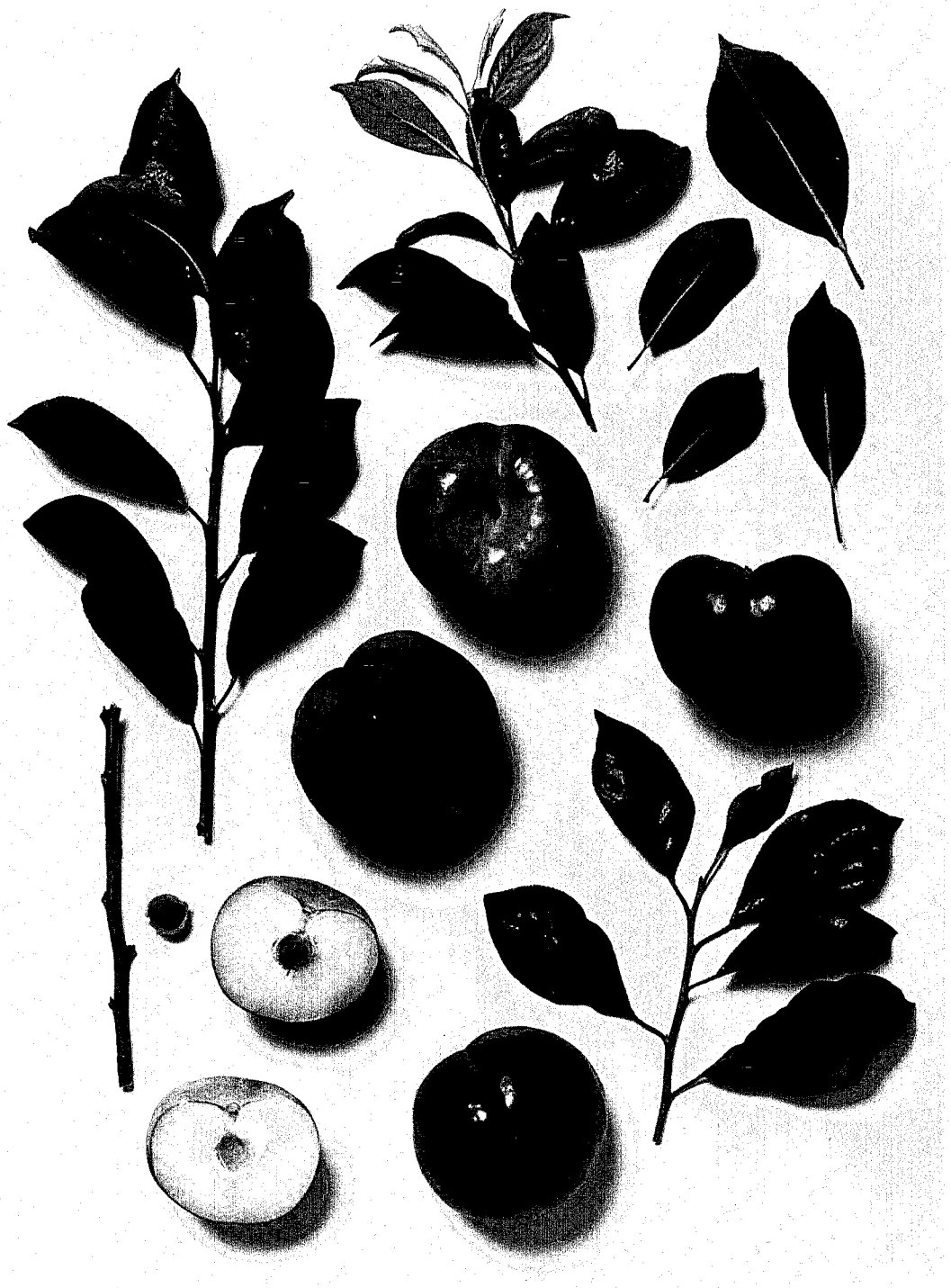

UNITED STATES PATENT AND TRADEMARK OFFICE

CERTIFICATE OF CORRECTION

PATENT NO. : Plant 8,057

DATED : December 8, 1992

INVENTOR(S) : Michael R. Gerawan

It is certified that error appears in the above-identified patent and that said Letters Patent is hereby corrected as shown below:

Column 3, Line 9, insert "Page" between Base- and 39

Signed and Sealed this

Nineteenth Day of October, 1993

*Attest:*

*Attesting Officer*

BRUCE LEHMAN

*Commissioner of Patents and Trademarks*